(12) United States Patent
You

(10) Patent No.: US 9,084,758 B2
(45) Date of Patent: Jul. 21, 2015

(54) **ANTIVIRAL COMPOSITIONS COMPRISING ETHANOL EXTRACT OF *TETRACERA SCANDENS* AND USE THEREOF**

(71) Applicant: The Catholic University of Korea Industry-Academic Cooperation Foundation, Seoul (KR)

(72) Inventor: Ji Chang You, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/467,610

(22) Filed: Aug. 25, 2014

(65) Prior Publication Data

US 2014/0370127 A1 Dec. 18, 2014

Related U.S. Application Data

(63) Continuation of application No. 13/852,321, filed on Mar. 28, 2013, now abandoned.

(30) Foreign Application Priority Data

Jul. 24, 2012 (KR) .................. 10-2012-0080407

(51) Int. Cl.
*A01N 65/00* (2009.01)
*A61K 36/185* (2006.01)
*A61K 36/00* (2006.01)

(52) U.S. Cl.
CPC ............... *A61K 36/185* (2013.01); *A61K 36/00* (2013.01); *A61K 2236/00* (2013.01)

(58) Field of Classification Search
CPC ..................................................... A61K 36/00
USPC ........................................................ 424/725
See application file for complete search history.

(56) References Cited

FOREIGN PATENT DOCUMENTS

KR 10-0979459 8/2010

OTHER PUBLICATIONS

Mai Thanh Thi Nguyen; Xanthine oxidase inhibitory activity of . . . ; Biol. Pharm. Bull. 27 (9); 2004; pp. 1414-1421.
Hyeok Sang Kwon, et al; Identification of anti-HIV and anti-reverse . . . ; BMB reports 2012; 45 (3); pp. 165-170; online published on Mar. 31, 2012.

*Primary Examiner* — Michael Meller
(74) *Attorney, Agent, or Firm* — Lucas & Mercanti, LLP

(57) ABSTRACT

A composition for preventing or treating a viral infection, which includes an ethanol extract of *Tetracera scandens* as an effective component, is provided. The composition exhibits low toxicity and few side effects and effectively inhibits reverse transcriptase activities to suppress synthesis of DNA, and thus can be useful in preventing or treating infections caused by various kinds of RNA viruses.

2 Claims, 4 Drawing Sheets

ANTIVIRAL COMPOSITIONS COMPRISING ETHANOL EXTRACT OF *TETRACERA SCANDENS* AND USE THEREOF

CROSS-REFERENCE TO RELATED APPLICATION

This application is a continuation of U.S. patent application Ser. No. 13/852,321, filed Mar. 28, 2013, which claims priority to and the benefit of Korean Patent Application No. 2012-0080407, filed Jul. 24, 2012, the disclosure of which is incorporated herein by reference in its entirety.

FIELD OF THE INVENTION

The present invention relates to an antiviral composition including an ethanol extract of *Tetracera scandens* as an effective component, and use thereof.

BACKGROUND OF INVENTION

RNA viruses are viruses having RNA as their genomes. Here, the RNA viruses have (+)-stranded RNA (positive sense RNA), complimentary (−)-stranded RNA (negative sense RNA), or double-stranded RNA, which is transcribed into mRNA, as their genomes. The (+)-stranded RNA may be translated to produce proteins when host cells are infected with the (+)-stranded RNA, and the (−)-stranded RNA is converted into (+)-stranded RNA by RNA polymerase, and then translated to produce proteins.

Therefore, an infection rate is high in the case of viruses having (+)-stranded RNA. Also, since RNA viruses have RNA as their genomes, there is no proof-reading done by DNA polymerase, which leads to a significant increase in mutagenesis compared with DNA viruses. As a result, new RNA viruses, such as SARS, hepatitis C, and polio, which cause diseases in humans, continue to appear, and there is a limit in producing vaccines against the new RNA viruses. In recent years, commercially available antiviral agents include nucleoside derivatives such as iododeoxyuridine (IDU), acyclovir (ACV) or azidothymidine (AZT), or proteins such as interferon (IFN). However, various side effects of the antiviral agents, for example, cytotoxicity, hepatotoxicity and drug resistance, have been reported. Therefore, there is a demand for development of a therapeutic agent for preventing or treating viral infections which has superior effects and few side effects.

Meanwhile, *Tetracera scandens* is a flowering plant which belongs to the *Dilleniaceae* family and grows mainly in Vietnam, and much research on its medical effects is being conducted. For example, it was reported that *T. scandens* has a pharmacological effect on an inflammatory response (Biol. Pharm. Bull. (2004) 27: 1414), and it was disclosed that a 4H-chromen-4-one derivative included in an extract of *T. scandens* serves to enhance glucose intake (Korean Patent No. 10-0979459). However, there is no report that *T. scandens* shows an antiviral effect by inhibiting reverse transcriptase activities of RNA viruses.

SUMMARY OF INVENTION

Therefore, the present invention is designed to solve the problems of the prior art, and it is an object of the present invention to provide a composition for preventing or treating a viral infection, which includes an ethanol extract of *Tetracera scandens* as an effective component.

However, the problems to be solved according to the present invention are not limited to the above-described problems, and the other problems which are not disclosed herein may be made apparent to those skilled in the art by the detailed description provided below.

One aspect of the present invention provides a composition for preventing or treating a viral infection, which includes an ethanol extract of *T. scandens* as an effective component.

According to one exemplary embodiment of the present invention, the ethanol may be 10% to 100% ethanol.

According to another exemplary embodiment of the present invention, the composition may inhibit reverse transcriptase activities of an RNA virus.

According to still another exemplary embodiment of the present invention, the virus is an RNA virus.

According to yet another exemplary embodiment of the present invention, the RNA virus may be selected from the group consisting of an influenza virus, a human immunodeficiency virus, a coronavirus, and tobacco mosaic virus.

BRIEF DESCRIPTION OF DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF INVENTION

Figure 1:
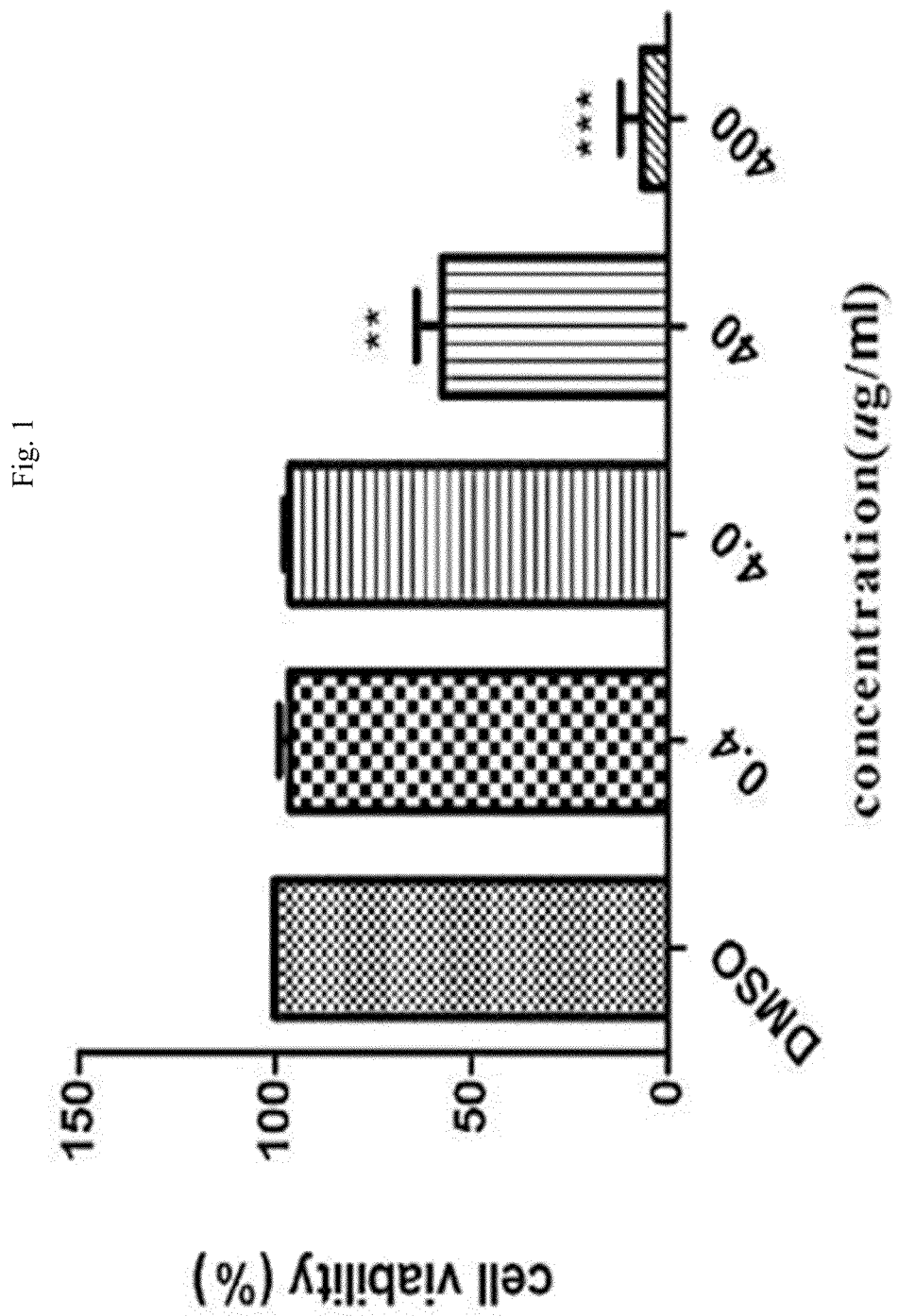
FIG. 1 is a diagram showing the results of confirming the cytotoxicity of an ethanol extract of *Tetracera scandens* using a GLO assay.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below.

The present inventors have conducted much research on a pharmaceutical composition for preventing and/or treating a viral infection, which has superior effects and few side effects. Therefore, the present invention was completed based on these facts.

To conduct research on pharmacological actions and effects of *Tetracera scandens* widely used for folk remedies, the present inventors obtained an ethanol extract by immersing *T. scandens* in ethanol.

According to one exemplary embodiment of the present invention, it is confirmed that the ethanol extract inhibits reverse transcriptase activities of viruses (see Example 4), and also that the ethanol extract exhibits no toxicity in a host cell and effectively inhibits reverse transcriptase activities of viruses to suppress growth of the viruses (see Examples 3 and 5).

From the results, the ethanol extract of *T. scandens* according to the present invention is expected to be applied to prevention and/or treatment of various kinds of infections of RNA viruses. Therefore, one aspect of the present invention provides a composition preventing and/or treating a viral infection, which includes the ethanol extract of *T. scandens* as an effective component. A concentration of the ethanol is not limited, but may be preferably in a range of 10% to 100%, more preferably 60% to 80%. Also, the composition is applicable to all kinds of RNA viruses using reverse transcriptase since the composition inhibits reverse transcriptase activities of viruses to suppress growth of the viruses. Preferably, the RNA virus may be an influenza virus, a human immunodeficiency virus, a coronavirus, or tobacco mosaic virus.

The composition according to the present invention may include a pharmaceutically available carrier. The pharmaceutically available carrier may include physiological saline, polyethylene glycol, ethanol, a vegetable oil, and isopropyl myristate, but the present invention is not limited thereto.

Another aspect of the present invention provides a method of treating a viral infectious disease. Here, the method includes administering a pharmaceutically effective amount of a composition including an ethanol extract of *T. scandens* as an effective component to a subject. In the present invention, the term "subject" refers to a patient in need of treatment of a disease, and, more particularly, a mammal such as a human, a non-human primate, a mouse, a rat, a dog, a cat, a horse, and cattle. In the present invention, it is also apparent to those skilled in the art that the pharmaceutically effective amount of the composition may be properly adjusted according to body weight, age, sex, and health condition of a patient, diet, an administration time, a method of administration, an excretion rate, and severity of a disease.

A desirable dose of the composition according to the present invention may vary according to conditions and body weight of a patient, severity of a disease, a type of a drug, a route of administration, and duration, and may be properly selected by those skilled in the art. However, the composition may preferably be administered daily at a dose of 0.001 to 100 mg/kg, and more preferably a dose of 0.01 to 30 mg/kg. The composition may be administered once a day, or administered in divided doses. The ethanol extract of *T. scandens* according to the present invention may be present at a content of 0.0001 to 10% by weight, preferably 0.001 to 1% by weight, based on the total weight of the composition.

The composition according to the present invention may be administered to a mammal such as a rat, a mouse, a domestic animal and a human through various routes of administration. A method of administration is not limited. For example, the composition may be administered orally, rectally, or by intravenous, intramuscular, subcutaneous, endocervical, or intracerebroventricular injection.

Hereinafter, preferred Examples are provided to aid in understanding the present invention. However, it should be understood that detailed description provided herein is merely intended to provide a better understanding of the present invention, but is not intended to limit the scope of the present invention.

EXAMPLES

Example 1

Preparation of Ethanol Extract of *T. scandens*

To prepare an ethanol extract of *T. scandens*, 30 to 40 g of *T. scandens* was immersed in 100 mL of 70% ethanol, and then cultured for 3 days. Thereafter, the cultured solution was put into a speed bag, and dried at 40° C. for 24 hours to prepare 200 g of an ethanol extract of *T. scandens*. Then, 500 µL of dimethyl sulfoxide (DMSO) was added per 40 mg of the prepared ethanol extract, which was then stored as a 20 µM concentrated solution.

Example 2

Confirmation of Cytotoxicity of Ethanol Extract of *T. scandens*

To confirm the cytotoxicity of the ethanol extract of *T. scandens*, the ethanol extract of *T. scandens* prepared in the same manner as in Example 1 was diluted with 0.5% DMSO to an increasing concentration of 0.4, 4, 40, and 400 µg/mL, and then treated with MT-4 cell line ($1 \times 10^4$ cells) as T-lymphocyte cells. Then, the resulting reaction mixture was cultured at 37° C. for 3 days under a 5% $CO_2$ condition, and cell viability was measured using a Cell Titer-Glo assay kit. A group of MT-4 cells treated only with 0.5% DMSO was used as the control. The results are shown in FIG. 1.

As shown in FIG. 1, it could be seen that the cytotoxicity was increasingly expressed according to a concentration of the ethanol extract of *T. scandens*. Also, it could be seen that, the ethanol extract of *T. scandens* exhibited no toxicity to cells when a concentration of the ethanol extract was equal to or less than 4 µg/mL, but approximately 90% of the cells died when the ethanol extract was present at a concentration of 400 µg/mL. Also, it was revealed that the ethanol extract of *T. scandens* had a mean $CC_{50}$ (50% cytotoxic concentration) value of 40 µg/mL.

Example 3

Measurement of Antiviral Activity of Ethanol Extract of *T. scandens*

Figure 2:
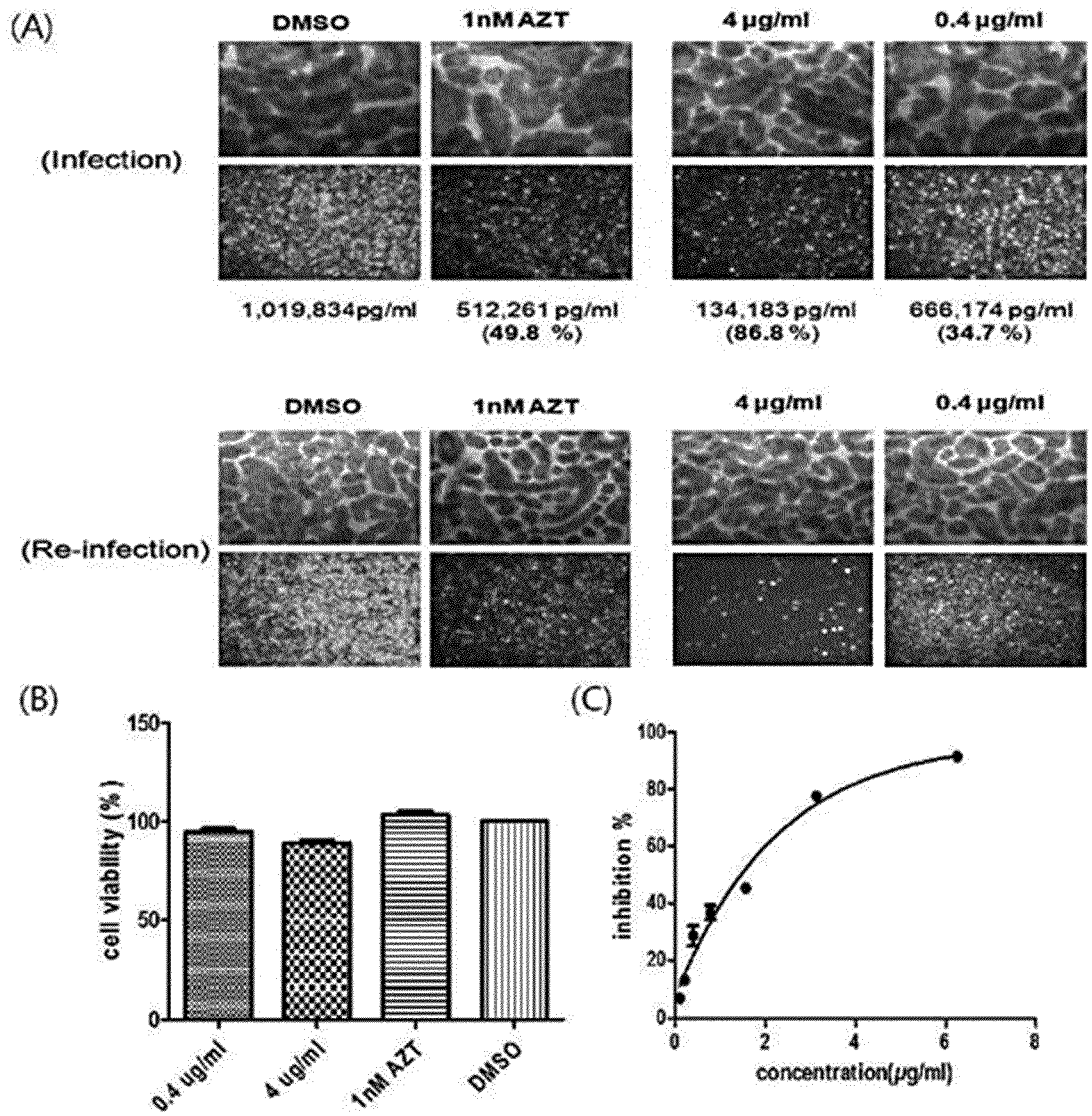
FIG. 2 is a diagram showing the results obtained by measuring the antiviral activities of the ethanol extract of *T. scandens*.

To measure the antiviral activities of the ethanol extract of *T. scandens*, an MT-4 cell line ($2 \times 10^5$ cells) was treated with the ethanol extract of *T. scandens* prepared in the same manner as in Example 1 at concentrations of 0, 0.4, and 4 µg/mL, infected with 20,000 pg of a human immunodeficiency virus (HIV) in which an Nef protein was substituted with an EGFP protein, and then cultured at 37 ° C. for 3 days under a 5% $CO_2$ condition. Thereafter, the cultured cells were centrifuged at 6,000 rpm for 3 minutes to obtain a cell pallet. Then, fluorescence intensity of a green fluorescence protein (GFP) secreted from the obtained cells was measured, a level of viral infection was confirmed using an HIV-1 p24 Antigen Capture Assay kit (Advanced BioScience Laboratories), and cell viability was determined using an MTT assay. 0.5% DMSO and 1 nM 3'-azido-3'-deoxy-thyminine (AZT) were used as the negative and positive controls, respectively. The results are shown in FIG. 2.

As shown in FIGS. 2A and 2B, it was revealed that the positive control which was treated with 1 nM AZT having no effect on cell viability exhibited an antiviral activity of 49.8%, and samples treated with 0.4 μg/mL and 4 μg/mL of the ethanol extract had antiviral activities of 34.7% and 86.8%, respectively. As shown in FIG. 2C, it was also revealed that the cytotoxicity was increasingly expressed according to a concentration of the ethanol extract of T. scandens, and the ethanol extract of T. scandens had an $IC_{50}$ (50% maximal inhibition concentration) value of 2.0 to 2.5 μg/mL. Also, it was revealed that the ethanol extract of T. scandens had an antiviral activity of substantially 100% when the ethanol extract was present at a concentration of 6 μg/mL.

Example 4

Confirmation of Effect of Ethanol Extract of T. scandens on Inhibition of Reverse Transcriptase Activity To determine how the ethanol extract of T. scandens exhibits the antiviral effect, an effect of the ethanol extract of T. scandens on inhibition of reverse transcriptase activities of viruses was confirmed. HIV reverse transcriptase (3 units) were treated with the ethanol extract of T. scandens at an increasing concentration of 0, 0.125, 0.25, 0.5, 1, 2, 4, 8, and 16 μg/mL and activities of HIV reverse transcriptase were measured using an Enzchek Reverse Transcriptase assay kit (Invitrogen). 0.5% DMSO was used as the negative control, and AZT, AZTTP, Efavirenz, and Etravirine were used as the positive controls. The results are shown in FIG. 3.

Figure 3:
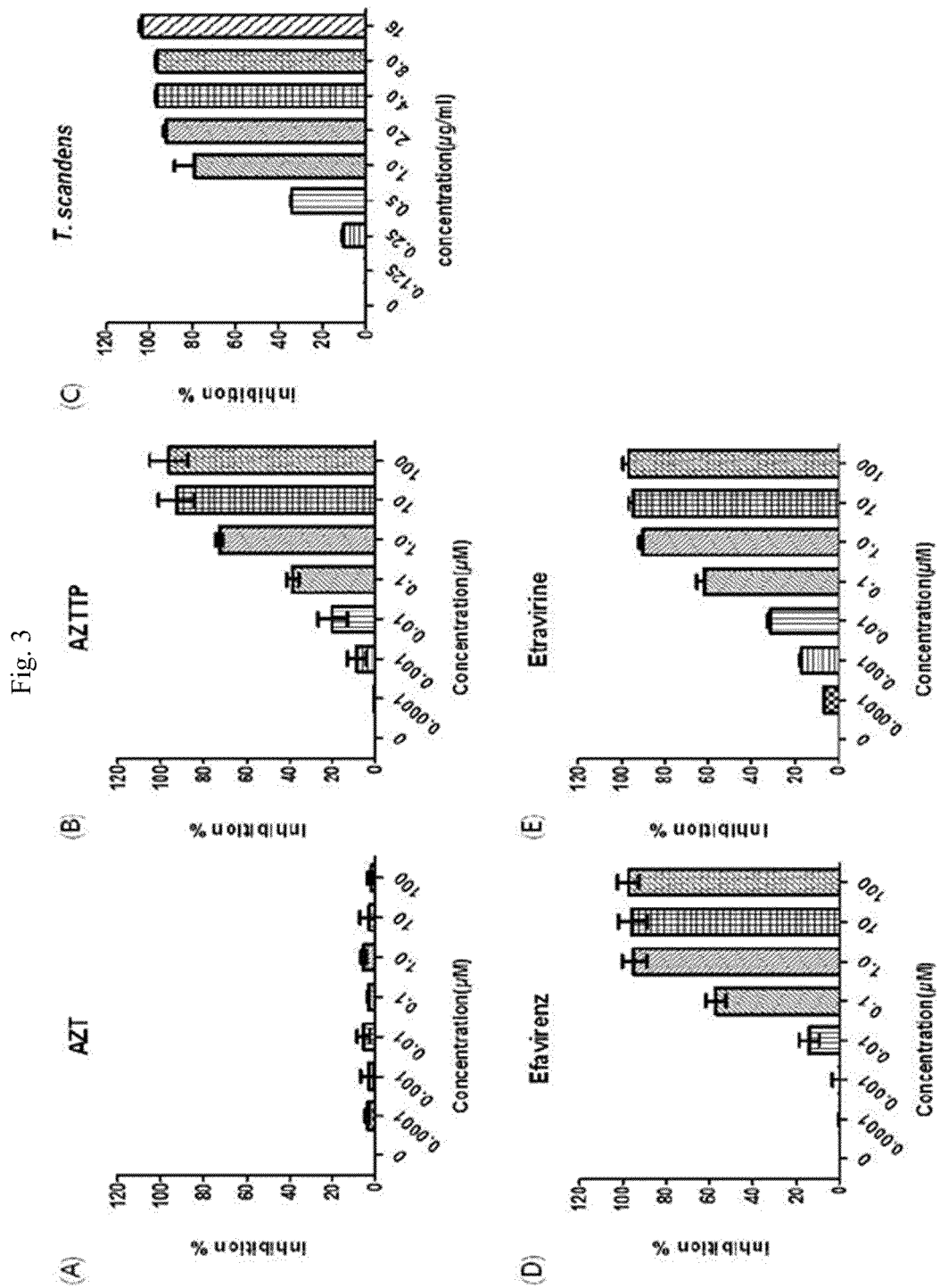
FIG. 3 is a diagram showing the results obtained by determining an effect of the ethanol extract of *T. scandens* on inhibition of reverse transcriptase activities.

As shown in FIG. 3, it could be seen that the activities of HIV reverse transcriptase were inhibited with an increase in concentration of the ethanol extract, and the ethanol extract of T. scandens showed an $IC_{50}$ value of 0.7 μg/mL. Also, it was revealed that the ethanol extract of T. scandens had an effect on inhibition of reverse transcriptase activities close to substantially 100% when the ethanol extract was present at a concentration of 4 μg/mL. It was revealed that, when AZTTP, Efavirenz, and Etravirine were used the positive control, the inhibition of the reverse transcriptase activities was increasingly expressed according to a concentration of the ethanol extract, but the reverse transcriptase activities were not inhibited when the ethanol extract was treated with unphosphorylated AZT. From the results, it was confirmed that the ethanol extract of T. scandens according to the present invention showed an antiviral effect by inhibiting the reverse transcriptase activities of RNA viruses.

Example 5

Confirmation of Effect of Ethanol Extract of T. scandens on Inhibition of Intracellular Reverse Transcriptase Activity To determine whether the ethanol extract of T. scandens effectively inhibits reverse transcriptase activities in cells, an MT-4 cell line ($5 \times 10^5$ cells) was treated with the ethanol extract of T. scandens prepared in the same manner as in Example 1 at concentrations of 0, 0.31, 0.63, 1.25, 2.5, 5, and 10 μg/mL, infected with 100,000 pg of HIV in which an Nef protein was substituted with an EGFP protein, and then cultured at 37° C. for 24 hours under a 5% $CO_2$ condition. Thereafter, DNA was extracted from the cultured cells using a DNeasy mini kit (Qiagen), and then subjected to quantitative DNA-polymerase chain reaction (PCR) using Light Cycler 480 (Roche), SYBR Green I Master mix (Roche) and HIV-1-specific LTR primers (Forward: 5'-GATCTGAGC-CTGGGAGCTCTC-3', and Reverse: 5'-CCTTTCGCTTTCAAGTCCCTGTTC-3') to quantify viral cDNA. The results are shown in FIG. 4.

Figure 4:
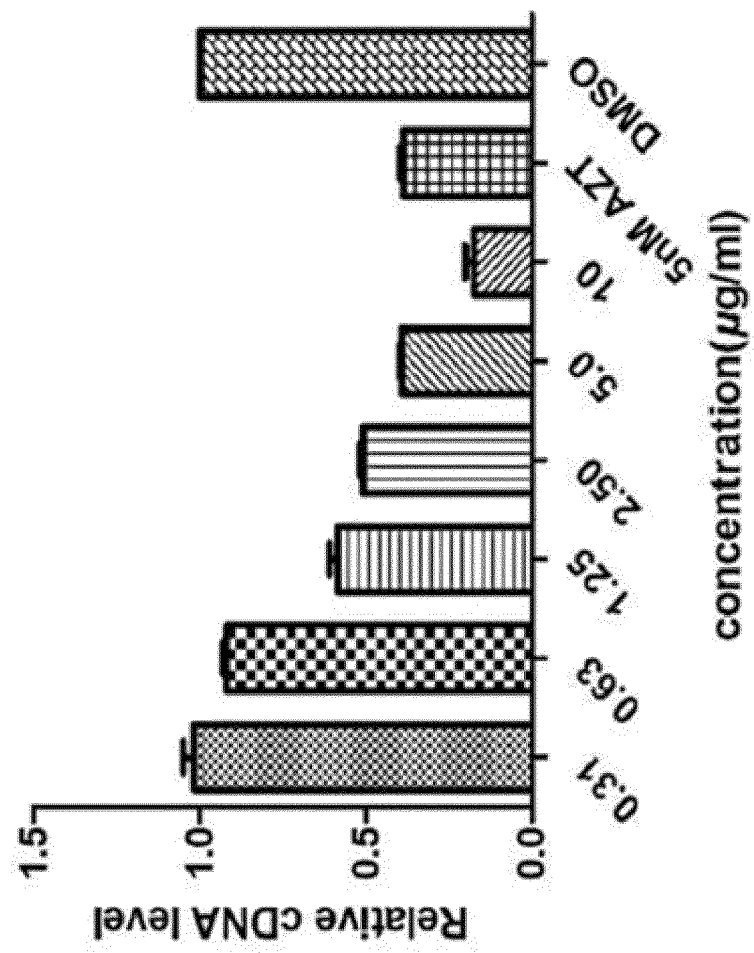
FIG. 4 is a diagram showing the results obtained by determining an effect of the ethanol extract of *T. scandens* on inhibition of intracellular reverse transcriptase activities.

As shown in FIG. 4, it could be seen that the cDNA synthesis in an RNA virus was decreased according to a concentration of the ethanol extract of T. scandens. Also, it could be seen that the cDNA synthesis was decreased by approximately 50% when the ethanol extract was present at a concentration of 2.5 μg/mL.

From the results, it could be seen that the ethanol extract of T. scandens according to the present invention inhibited the synthesis of cDNA by effectively inhibiting the reverse transcriptase activities of the RNA virus in the cells, thereby inhibiting growth of the RNA virus. As a result, it was revealed that the ethanol extract of T. scandens according to the present invention was able to be used to prevent or treat a viral infection.

The present invention provides a composition for preventing or treating a viral infection, which includes the ethanol extract of T. scandens as an effective component. More particularly, the present invention provides a pharmaceutical composition including an ethanol extract of T. scandens, which is able to be used to prevent or treat diseases caused by a viral infection since the ethanol extract of T. scandens functions to inhibit the reverse transcriptase activities of viruses. The ethanol extract of T. scandens according to the present invention has low toxicity and few side effects since the ethanol extract is a plant extract, and is expected to be widely used to prevent and/or treat diseases caused by various kinds of RNA viruses since the ethanol extract effectively inhibits reverse transcriptase activities to suppress synthesis of DNA.

While the invention has been shown and described with reference to certain exemplary embodiments thereof, it will be understood by those skilled in the art that various changes in form and details may be made therein without departing from the scope of the invention as defined by the appended claims.

What is claimed is:

1. A method for treating a viral infection in a human or animal in need thereof comprising:
   administering to said animal or human in need thereof a therapeutically effective amount of a composition comprising an ethanol extract of *Tetracera scandens* to treat the viral infection in the human or animal in need thereof.

2. The method of claim 1, wherein the ethanol is 10% to 100% ethanol.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: LTR primer F1

```
<400> SEQUENCE: 1
gatctgagcc tgggagctct c                                              21

<210> SEQ ID NO 2
<211> LENGTH: 24
<212> TYPE: DNA
<213> ORGANISM: Artificial Sequence
<220> FEATURE:
<223> OTHER INFORMATION: LTR primer R1

<400> SEQUENCE: 2
cctttcgctt tcaagtccct gttc                                           24
```